(12) United States Patent
Sieller et al.

(10) Patent No.: US 7,048,704 B2
(45) Date of Patent: *May 23, 2006

(54) ORTHOTIC DEVICE

(76) Inventors: Richard T. Sieller, 1220 Sycamore Rd., Virginia Beach, VA (US) 23452; Ronald B. Hopkins, 509 Cheswick Arch, Virginia Beach, VA (US) 23455

( * ) Notice: Subject to any disclaimer, the term of this patent is extended or adjusted under 35 U.S.C. 154(b) by 505 days.

This patent is subject to a terminal disclaimer.

(21) Appl. No.: 10/348,457

(22) Filed: Jan. 21, 2003

(65) Prior Publication Data

US 2003/0144620 A1 Jul. 31, 2003

Related U.S. Application Data

(63) Continuation-in-part of application No. 09/964,636, filed on Sep. 28, 2001, now Pat. No. 6,537,237.

(51) Int. Cl.
*A61F 5/00* (2006.01)
(52) U.S. Cl. .......................... 602/16; 602/26
(58) Field of Classification Search ............... 602/16, 602/23–27; 128/882
See application file for complete search history.

(56) References Cited

U.S. PATENT DOCUMENTS

| | | | |
|---|---|---|---|
| 2,195,024 A * | 3/1940 | Bullock | 602/26 |
| 4,100,918 A | 7/1978 | Glancy | |
| 4,191,373 A | 3/1980 | Lancellotti | |
| 4,408,600 A | 10/1983 | Davis | |
| 4,606,542 A * | 8/1986 | Segal | 482/124 |
| 4,682,776 A * | 7/1987 | Mitchell et al. | 473/63 |
| 4,763,901 A | 8/1988 | Richter | |
| 4,805,606 A | 2/1989 | McDavid, III | |
| 4,838,251 A | 6/1989 | Chignon et al. | |
| 4,862,878 A | 9/1989 | Davison et al. | |
| 4,865,024 A * | 9/1989 | Hensley et al. | 602/16 |
| 5,020,525 A | 6/1991 | Ewing et al. | |
| 5,117,814 A | 6/1992 | Luttrell et al. | |
| 5,167,612 A | 12/1992 | Bonutti | |
| 5,213,094 A * | 5/1993 | Bonutti | 601/33 |
| 5,337,737 A | 8/1994 | Rubin et al. | |
| 5,352,190 A | 10/1994 | Fischer et al. | |
| 5,365,947 A * | 11/1994 | Bonutti | 128/898 |
| 5,383,845 A | 1/1995 | Nebolon | |
| 5,437,611 A | 8/1995 | Stern | |
| 5,503,619 A | 4/1996 | Bonutti | |
| 5,611,764 A | 3/1997 | Bonutti et al. | |
| 5,683,336 A | 11/1997 | Pape | |
| 5,685,830 A | 11/1997 | Bonutti | |
| 5,857,988 A * | 1/1999 | Shirley | 602/26 |
| 5,865,714 A | 2/1999 | Marlowe | |
| 5,891,079 A | 4/1999 | Barnes | |
| 6,063,048 A | 5/2000 | Bodenschatz et al. | |
| 6,113,562 A | 9/2000 | Bonutti et al. | |
| 6,117,097 A | 9/2000 | Ruiz | |

* cited by examiner

*Primary Examiner*—Michael A. Brown
(74) *Attorney, Agent, or Firm*—John H. Thomas, P.C.

(57) ABSTRACT

An orthotic device has first and second, elongated support members. The support members are pivotally connected at their respective proximal ends. The device further includes a tensioning member. There are also first, second and third pairs of guides, each pair adapted to receive the tensioning member. Whereby the device may facilitate movement of a limb into either a flexed or extended position by placing the tensioning member in the first and second or second and third pairs of guides respectively.

11 Claims, 8 Drawing Sheets

ORTHOTIC DEVICE

This application is a continuation-in-part of application Ser. No. 09/964,636 now U.S. Pat. No. 6,537,237, filed Sep. 28, 2001.

The present invention relates to an orthotic device able to apply dynamic or static forces to a joint in need of therapy. The combination of components acts to provide multiple functions through the variable positioning of selected components. The force generated by the components and their direction can be quantified and used in therapeutic treatment to provide treatment guidelines.

BACKGROUND OF THE INVENTION

There are many known orthotic devices including those specifically directed to rehabilitation of various joints such as elbows, knees, wrists and ankles. Typically, these apparatuses are static or have a single pressure/force that is applied during operation. Those forces may be uneven across the device. Usually, the forces are focused solely on extension or flexion, but not both.

One problem with conventional devices is the inability to easily customize those devices for a particular patient. A given arrangement may be useful and appropriate for one patient, but not as effective for another. Further, those devices may be difficult to adjust between, for instance, flexion or extension. Also, typical devices are not able to easily vary their tension and quantify such for a given patient. For instance, a weak or frail patient may require less tension or force during therapy than a large or strong patient. Also, as a patient gains strength during therapy, the device needs to be able to be variable as the therapy process moves forward.

SUMMARY OF THE INVENTION

Accordingly, it is an object of the present invention to overcome the forgoing drawbacks and problems. The present invention provides a combination of components that provide multiple functions and can be arranged to produce varied directional forces. The forces generated by the present device can be quantified and used in therapeutic treatment to provide treatment guidelines.

In one embodiment, the orthotic device comprises first and second limb support members which are pivotally connected at their respective proximal ends. The orthotic device further includes tensioning means and a first center post positioned at the distal end and at substantially the middle of the first member. There is also a second center post adapted to receive the tensioning member and positioned at the distal end and at substantially the middle of the second member. First and second pairs of guides are adapted to receive the tensioning member. The first pair of guides is positioned at the distal end of the first member and at opposite sides of the first member. The second pair of guides is positioned at the proximal end of the second member and at substantially the middle of the member. The first and second pairs of guides are positioned so that when the tensioning member is placed in the first guides and around the second center post, a flexion moment is created; and when the tensioning member is placed around both the first and second center posts and in the second guides, an extension moment is created. Accordingly, when the device is fitted to a patient's limb connected by a joint, the limb can be urged to either a flexed or extended position by placing the tensioning member in the first or second guides respectively. The tensioning member may further comprise means for varying the length of the tensioning member. The second center post may comprise a pulley. The pulley may further comprise a tension gauge that measures and displays the amount of tension exerted by the tensioning member. The tensioning member can be a single, noncontinuous piece that is releaseably secured at each end to the first center post. The pivotable connection between the support members may comprise a range of pivot limiter.

In a further embodiment, an orthotic device comprises first and second elongated support members, wherein the support members are pivotally connected at their respective proximal ends. The device further includes a tensioning member and first and second post means for retaining the tensioning member at the distal ends of the first and second members respectively. There are also first and second pairs of means for guiding the tensioning member. The first pair of guide means is positioned at the distal end of the first member and on opposite sides of the member. The second pair of guide means is positioned at the proximal end of the second member and at substantially the middle of that member. When the tensioning member is placed in the first pair of guide means and around the second post means, a flexion moment is created; and when the tensioning member is placed around both the first and second post means and in the second pair of guide means, an extension moment is created. Therefore, when the device is fitted to a patient's limb connected by a joint, the limb can be urged to either a flexed or extended position by placing the tensioning member in the first or second guide means respectively. The tensioning member may further comprise means for varying the length of the tensioning member. The second post means may comprise means for equalizing tension along the tensioning member. The tension equalizing means may further comprise a tension gauge that measure and displays the amount of tension exerted by the tensioning member. The tensioning member can be a single, noncontinuous piece that is releasably secured at each end to the first post means. The second post means may comprise a means for equalizing tension along the tensioning member. The pivotal connection between the support members may comprise a range of pivot limiter.

In a still further embodiment, an orthotic device comprises first and second elongated support members, wherein the support members are pivotally connected at their respective proximal ends. The device further comprises a tensioning member and a plurality of guides adapted to receive the tensioning member wherein the guides allow a user to change the directional force created by the tensioning member on the support members.

In an alternative embodiment, an orthotic device comprises first and second elongated support members. The support members are pivotally connected at their respective proximal ends by a pair of hinges mounted substantially on opposite sides of the support members. Each of the support members comprises anterior and posterior portions with respect to a plane passing through the hinges. The device further comprises a tensioning member and three pairs of guides. The first pair of guides is positioned on the first member and at opposite sides of the first member. The second pair of guides is positioned on the second member and at opposite sides of the second member. The third pair of guides is positioned on the first member near the proximal end of the first member and on the anterior portion of the first member. When the tensioning member is placed in the first and second pairs of guides only, a flexion moment is created. When the tensioning member is placed in the second and third pairs of guides only, an extension moment is created. A tensioning member may be a single, noncontinuous piece secured at each end to a support member. The tensioning member could be a loop. There may be included means for varying the length of the tensioning member. The tensioning member may be an elastic cord. The device may further comprise a static cord connected to the support members and adapted to limit the range of pivot of the support members. The hinges may comprise range of pivot limiters. The third pair of guides may be pulleys or all of the guides may be pulleys.

In a further alternative embodiment, an orthotic device may comprise first and second elongated support members, wherein the support members are pivotally connected at their respective proximal ends. The device further comprises a tensioning member. It further comprises a plurality of guides including at least a first pair of guides, the plurality of guides positioned on the support members and adapted to receive the tensioning member. The first pair of guides is mounted on opposite sides of a support member, wherein the plurality of guides permit a user a change the directional force created by the tensioning member on the support members. The tensioning member may be loop or it may be a single, noncontinuous piece secured at each end to a support member. The device may further comprise means for varying the length of the tensioning member. The tensioning member may be an elastic cord. Also, all of the guides may be pulleys.

In still further embodiments, the invention includes orthotic device kits for each of the foregoing device embodiments. In each case, the kit would include a set of each of the components or sub combinations of components of the devices described herein.

DETAILED DESCRIPTION OF THE PREFERRED EMBODIMENTS

Figure 1:
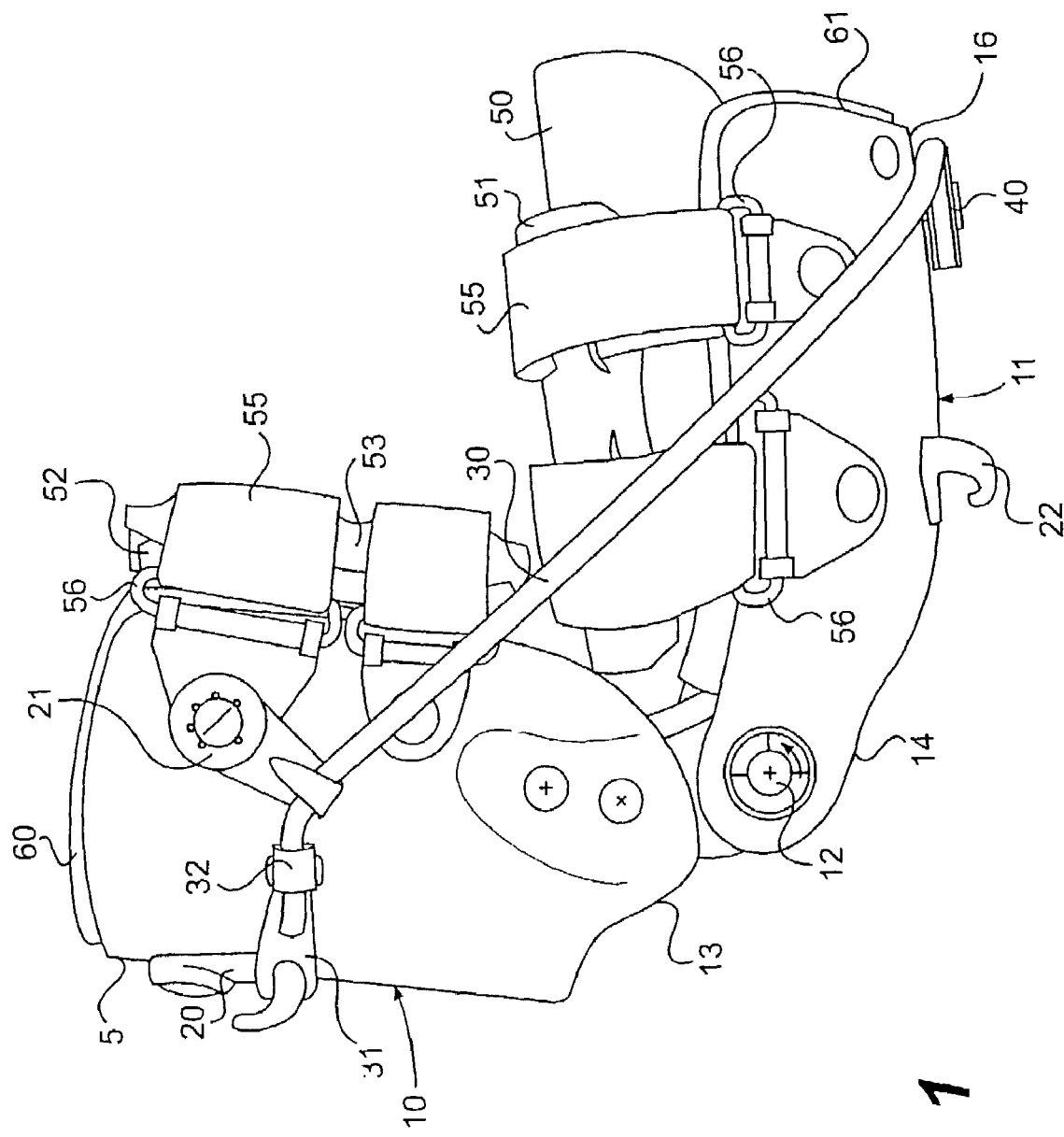
FIG. 1 is a side elevation view of one embodiment of a device in accordance with the present invention with the device shown in a flexed position.

The present invention is intended for use with a joint such as an elbow, knee, wrist or ankle. The specific embodiment shown in FIGS. 1 through 4 describes an elbow brace. Of course, the teachings may be applied to other devices for other joints in accordance with the present teachings.

The elbow brace shown in FIGS. 1 through 4 includes a first limb support member 10 and a second limb support member 11. These particular support members are elongated cuffs made primarily of a stiff plastic material. The support members 10 and 11 will typically come in different sizes to fit different sized arms. It is also possible that an orthotic device may be custom molded to accurately fit a specific arm of a given patient.

The first member 10 is adapted to support an upper arm. The first member 10 has a proximal end 13 adjacent the second member 11 and a distal end 15 on the opposite end of the elongated first member 10. The second member 11 is adapted to support a forearm. It is made up of a proximal end 14 adjacent the first member 10 and a distal end 16. Both the first and second members 10 and 11 are roughly in the shape of a half tube adapted to wrap a substantial way around a patient's limb to support it. The proximal ends 13 and 14 are connected by a hinge 12 in order to allow the device to flex and extend with the limb being braced. The hinge 12 defines the mechanical axis of rotation of the brace. The anatomical axis of the limb (in this example an elbow) will be approximately the same as the mechanical axis of the brace.

A person's limb, in this case an arm, is held within the device by straps 55 that connect the opposite sides of the respective first and second members 10 and 11. The straps 55 extend from one side of the members 10 and 11 across through a loop 56 and back onto themselves. The straps 55 are preferably made from conventional hooks and loops (Velcro) to secure the person's limb within the device. Soft plastic sleeves 50 and 52 are positioned inside the straps 55 through use of pads 51 and 53 in order to better secure the patient's limb and to make the device more comfortable overall. Additionally, pads 60 and 61 may line the insides of the first and second members 10 and 11 to add in the comfort and fit of the brace.

The device as described thus far is conventional. The sleeve elements and the straps and a hinge assembly are all used with various alternatives in the construction of limb braces/orthotic devices generally. The following teachings with respect to the positioning and variability of a tensioning means may be applied to any of these conventional type braces whether or not the underlying components are exactly as described herein thus far.

A tensioning means 30 can be any type of elastic member including a rubber cord, plastic or metal spring, or any other type of elastic member. As shown in the drawings, the tensioning means 30 is a rubber cord or bungee cord. The tensioning means 30 is a single noncontinuous piece, but it could alternatively be a continuous loop. Also, more than one elastic member can make up a tensioning means. The tensioning means 30 has ends 31 that are attached to a tensioning member through clamps 32. Alternatively, instead of a permanent clamp 32, there may be an adjustable piece 35 that allows the tensioning means 30 to be lengthened or shortened. This length adjuster piece 35 can be simply two slots or can be any other type of adjustable clamping mechanism. The ends 31 further have holes that are adapted to hook over to latch onto two retaining hooks 20. The retainer hooks 20 may be one or, as shown, a pair of hooks. They may be any other type of post or other anchoring device to engage and hold the ends 31 of the tensioning member 30. The retainer hooks 20 or other type of post should be positioned on the outer surface of and in approximately the center or middle of the distal end 15 of the first member 10.

Figure 4:
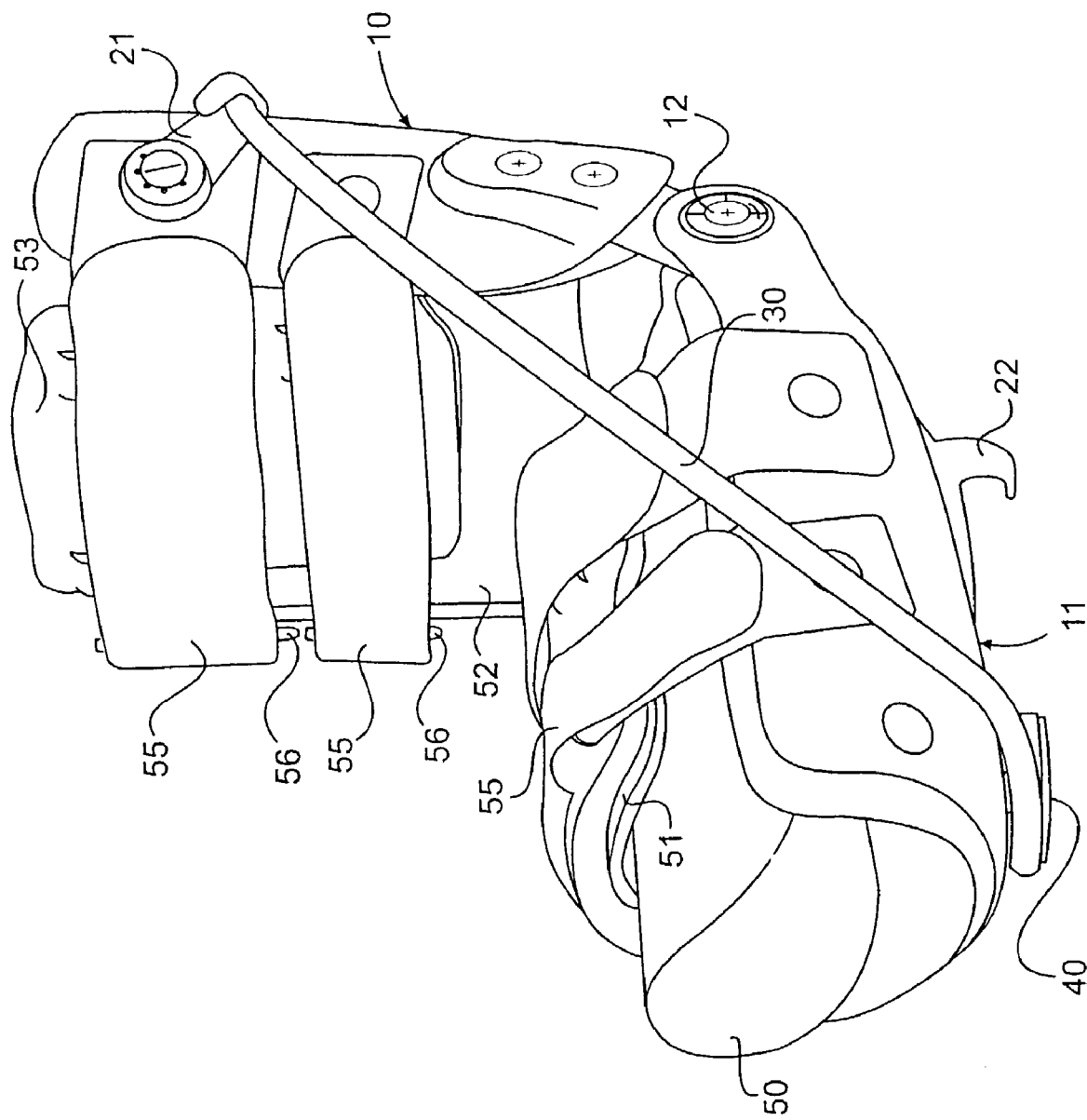
FIG. 4 is a perspective view of one embodiment of a device in accordance with the present invention with the device shown in a flexed position.

When in the flexed positioned as shown in FIGS. 1 and 4, the tensioning means 30 loops through the pair of guides 21 and around pulley 40. When the tensioning member is the appropriate length, it will create a steady and constant force urging the arm within the device into the flexed position. By varying the length of the tensioning means 30, the amount of tension urging the device/patient's limb into the flexed position may be varied. The guides 21 are simply hooks like hooks 20. The retainer hooks 20 are positioned on the outer surface and at the distal end of the first member 10 in approximately the center or middle of the member. The guides 21 are positioned at the distal end of the first member, but on opposite sides of the retainer hooks 20. The pulley 40 is positioned at the distal end 16 of the second member 11 and substantially at the middle of the second member.

Figure 2:
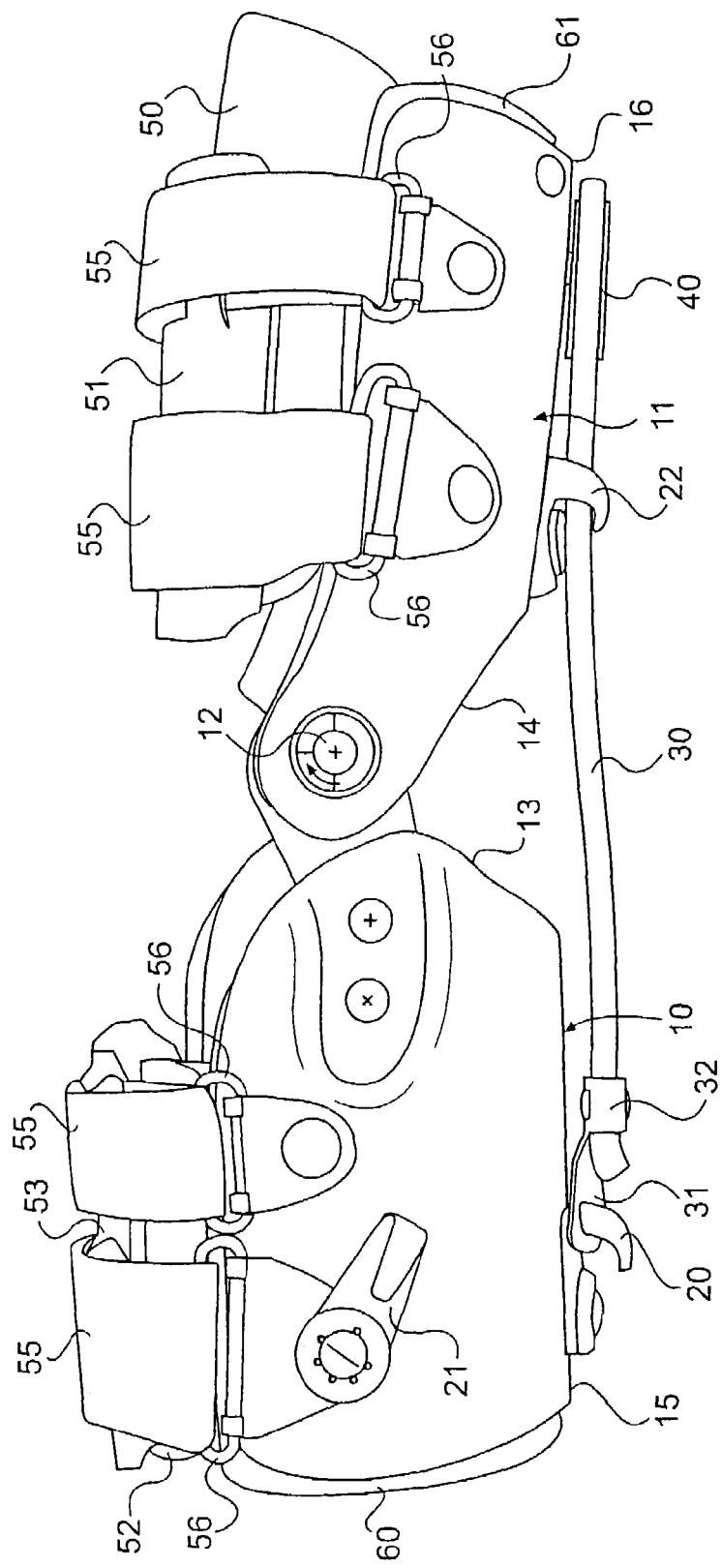
FIG. 2 is a side elevation view of one embodiment of a device in accordance with the present invention with the device shown in an extended position.
Figure 3:
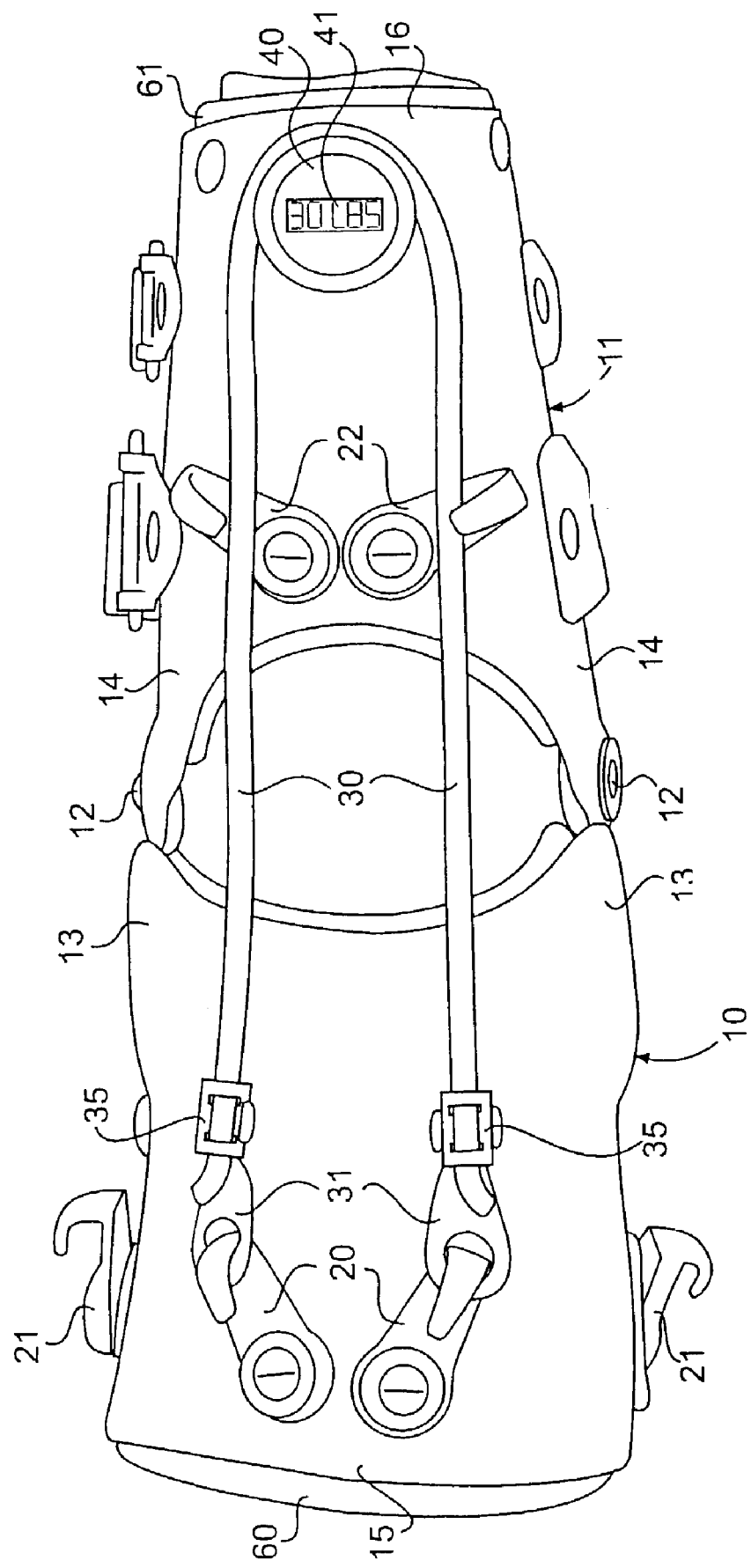
FIG. 3 is a top elevation view of one embodiment of a device in accordance with the present invention with the device shown in an extended position.

In the extended position as shown in FIGS. 2 and 3, the tensioning means 30 is attached to the retainer hooks 20 and looped around the pulley 40. The tensioning means 30 is further placed within the guides 22. The guides 22 are positioned on the outer surface and in the middle of the proximal end 14 of the second member 11. In this way, the device is pulled to the extended position.

As illustrated in the alternative figures, the brace may be urged to the extended or flexed position by placement of the tensioning means 30 within guides 21 (flexed position) or guides 22 (extended position). For ease of use, the guides 21 and 22, as well as the retainers 20 are hooks. Other types of retainers or guides may be used to receive and hold the tensioning means 30 so that it is urging the brace in the flexed or extended positions. Also, as noted earlier, the tensioning means 30 may be a continuous loop. Placement of the tensioning means 30 as described above is equally applicable to a continuous loop. The primary difference is that a center post (either one or more) rather than retainer hooks 20 can be used to hold a tensioning member about the center (middle) of the distal end of the second member. Similarly, if the tensioning means 30 is a plurality of elastic members, then the device designer will use the teachings herein to position a sufficient number of posts and/or hooks to achieve the same or similar results obtained herein.

The precise placement of the guides 21 or 22 will be a matter of choice by a given therapist. As shown, the guides 21 and 22 (as well as the center post 20) are hooks that are attached by screws to the first and second limb members 10 and 11. Generically speaking, guides or posts may be mounted in slots that allow a therapist to move the guides or post on the members. There may also be predrilled holes to receive the screws that anchor the guides or posts in the member. In operation, it is only essential that the guides 21 in conjunction with the pulley 40 (or any center post at the distal end of the second member 11) create a force that causes a flexion moment. That is, the force of a tensioning member must be on the correct side of the anatomical/ mechanical axis to draw the ends of the members towards each other in a flexion or extension rotation. Accordingly, the guides 21 that position the tensioning member 30 so that it causes a flexion moment are oriented on the side of the anatomical and mechanical axes to create that flexion moment. The alternative to the flexion moment is the creation of an extension moment where the tensioning member 30 is oriented along the center of the members 10 and 11 and on the outside of the anatomical/mechanical axis of the brace when worn by a user. (For the purposes of this relative discussion, from a side view, the "outside" is the side having the members 10 and 11, and the "inside" is the side having the straps 55). The guides 22 are relatively centered as are the retaining hooks 20 (or any center post) and pulley (any center post). As shown in FIG. 2, therefore, the tensioning means is on the outside of the anatomical/ mechanical axis and therefore creates an extension moment. In order to create a flexion moment force, guides such as guides 21 will be positioned on the opposite and relatively inside of a brace, while the extension guides such as guides 22 will be oriented along the center or outside of a brace.

The pulley 40 is a tension equalizing device in that it equalizes the forces of the tensioning member 30 on each side of the device. This allows for balanced and equal forces in therapy. While a pulley 40 is envisioned as preferable, any post centered at the distal end 16 of the second member 11 can work. For instance, a smooth or low friction post in combination with a low friction surface on a cord could also allow equalization of the tension along the cord. Also, as best seen in FIG. 3, the pulley 40 can have engineered into it a tension gauge 41 that measures and displays the amount of tension being exerted by the tensioning member 30. The tension gauge 41 may be used in conjunction with the length adjustor piece 35 in order to accurately apply a given tension pressure to a joint when the device is used in therapy. In other words, a therapist may want a very slight tension on a very painful joint. On the other hand, it may be desirable to exert a substantial tension in order to help straighten or bend a joint. By quantifying the amount of tension, a therapist is able to better monitor and control the specific therapy that is preferably administered for a given patient. These tension gauges are referred to as economy force gauges commercially available from McMaster-Carr, Inc.

Another alternative feature of the present invention includes the use of a range of pivot limiter in the hinge 12. By limiting the range of the pivot through known limiting devices, the patient's joint can be protected from abnormal force, preventing extreme range of motion and protecting from injury or damage to surgically placed registration. The use of this range of motion or range of pivot limiter with the hinge 12 is a still further therapy device that, particularly when combined with the tensioning member and guides discussed earlier, allows a therapist to deliver exactly a quantifiable and repeatable therapy to a joint. A therapist can prescribe and limit a specific range of motion and/or amount of tension, thereby removing the guess work from the therapy.

The example discussed in connection with the figures displays the pulley 40 on the relatively lower limb member 11 and the retaining hooks 20 on the relatively upper limb member 10. The placement of these components can be reversed with the other posts and guides being moved to similar opposite locations on the respective limb members.

A still further variation of the present invention is an orthotic device kit. This kit would include all of the parts described herein. Specifically, there would be first and second limb support members pivotally connectable at their respective proximal ends. There are first and second central tension receiving means. The first member would be adapted for affixing thereto, at substantially at the middle of its distal end, the first central tension receiving means. The second member is adapted for affixing thereto, at substantially at the middle of its distal end, the second central tensioning receiving means. The kit would further include first and second pairs of guides, each pair adapted to guide the tensioning means. The first member adapted for affixing thereto the first pair of guides at opposite sides of its distal end. The second member adapted for affixing thereto the second pair of guides at substantially the middle of its proximal end, wherein with the tensioning means positioned in the affixed first guides and received in the affixed second central means, a flexion moment is created; and with the tensioning means positioned in both the first and second affixed central means and in the fixed second guides, an extension moment is created. In summary, therefore, the kit is merely the separate list of components like those shown in FIGS. 1–4 but before their assembly.

FIGS. 5–8 display a knee brace in an alternative embodiment of the present invention. The brace includes elongated support members 100 and 101. These support members 100 and 101 are elongated cuffs made primarily of a stiff plastic material. Both the first and second support members 100 and 101 are roughly in the shape of a half tube adapted to wrap a substantial way around a patient's limb to support it. As shown, support member 100 is adapted to receive the back side or posterior portion of a person's upper leg or thigh. Support member 101 is adapted to receive the front or anterior side of a person's lower leg or shin. The support members 100 and 101 will come in different sizes to fit different sized legs. It is possible that an orthotic device may be custom molded to accurately fit a specific leg of a given patient. Also, it is possible that the rigid cuff portions could cover the anterior portion of the thigh or posterior portion of the lower leg as opposed to the brace that is shown. Still further, both cuff portions could be anterior or posterior. The support members 100 and 101 have proximal ends 103 and 104 respectively. The proximal ends 103 and 104 are connected by a hinge 102 in order to allow the device to rotate or flex and extend with the leg being braced. The hinge 102 defines the mechanical axis of rotation of the brace. The anatomical axis of rotation of the leg (knee) will be approximately the same as the mechanical axis of rotation of the brace. Preferably, therefore, the hinges are mounted substantially on opposite sides of the support member, but there could be some variation with respect to the specific location.

A patient's leg is held within the brace by straps 110 that connect the opposite sides of the respective support members 100 and 101. The straps 110 extend from one side of the members 100 and 101 and through a loop 111 and back onto themselves. The straps 110 are preferably made from conventional hook and loop construction to secure the person's leg within the brace. In FIGS. 5–8, a person's leg and foot is shown in broken lines.

A tensioning member 115 is used to create both flexion and extension moments in the device. The tensioning member 115 can be any type of elastic member including a rubber cord, plastic or metal spring. As shown in the drawings, the tensioning member 115 is a bungee cord. The tensioning member is a single, noncontinuous piece, but it could alternatively be a continuous loop. As shown, a tensioning member 115 is fixed on one end to member 101 by anchor 116. On the other end of tensioning member 115, there is a clamp 117 that receives the tensioning member and holds it in place. The clamp 117 is fixed to member 101 and is adapted to allow the tensioning member 115 to be removably mounted therein. In this way, the length of the tensioning member 115 may be varied in order to vary the tension created and the flexion and extension moments that result therefrom.

Although the tensioning member 115 is preferably elastic, it is also possible that the tensioning member is an inelastic, static cord. A static cord could be used in an alternating manner with an elastic cord during therapy. Still further alternatively, a static cord could be used concurrently with an elastic cord. In this combination, the elastic cord would apply a dynamic force in the direction of flexion or extension, while the static cord could effectively limit the range of pivot of the support members. The static cord could be a strictly separate cord from an elastic cord, or the tensioning member could be a hybrid cable that has a specific amount of elasticity before an integral, static component would prevent further elastic movement. Therefore, for the purposes of this application, a "tensioning member" is defined as an elastic cord, an inelastic (static) cord, and/or hybrids and combinations thereof.

Figure 6:
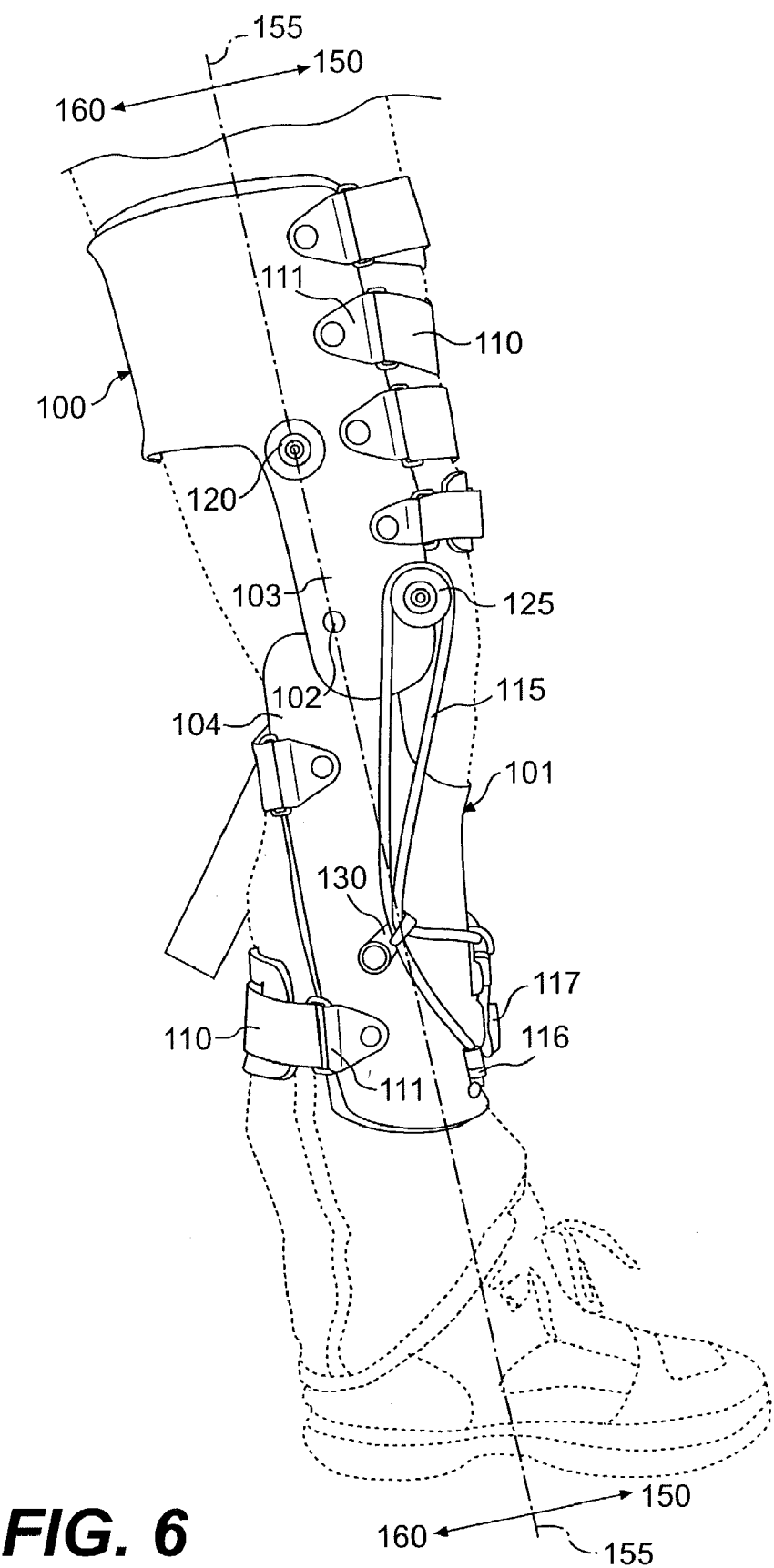

Referring specifically to FIG. 6, there is shown the anterior portion 150 and posterior portion 160 of each of the support members 100 and 101 of the brace. As shown, when the brace is in a substantially extended position as shown (i.e., in generally a straight line), a plane designated by the broken line 155 passes through the hinge 102 to separate the brace between the front or anterior portion 150 and the back or posterior portion 160. This plane 155 is commonly referred to as the sagittal plane.

Figure 7:
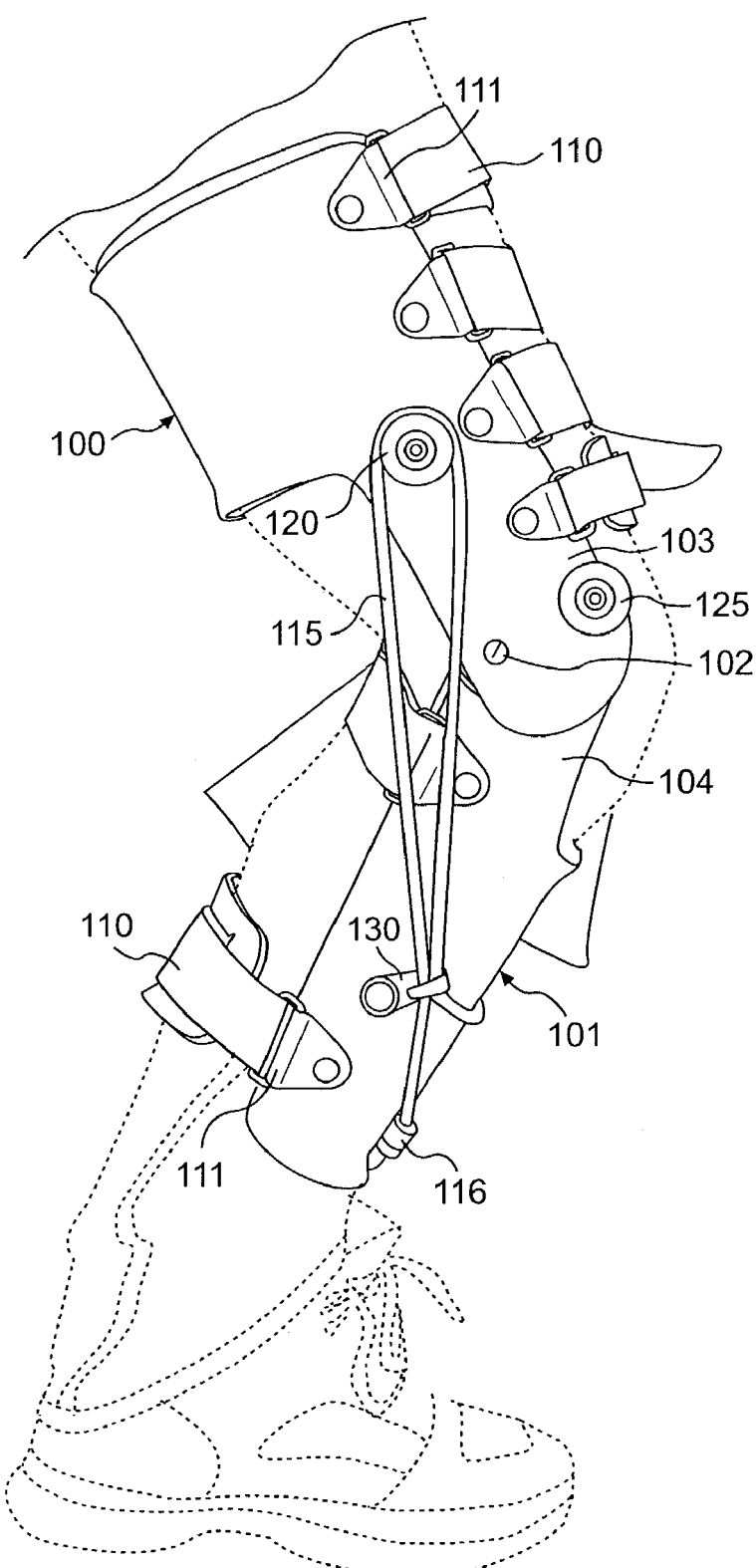
FIGS. 7 and 8 are side and front elevation views respectively of an alternative embodiment of a device in accordance with the present invention with the device shown in a position that creates a flexion moment on a limb in the device.
Figure 8:
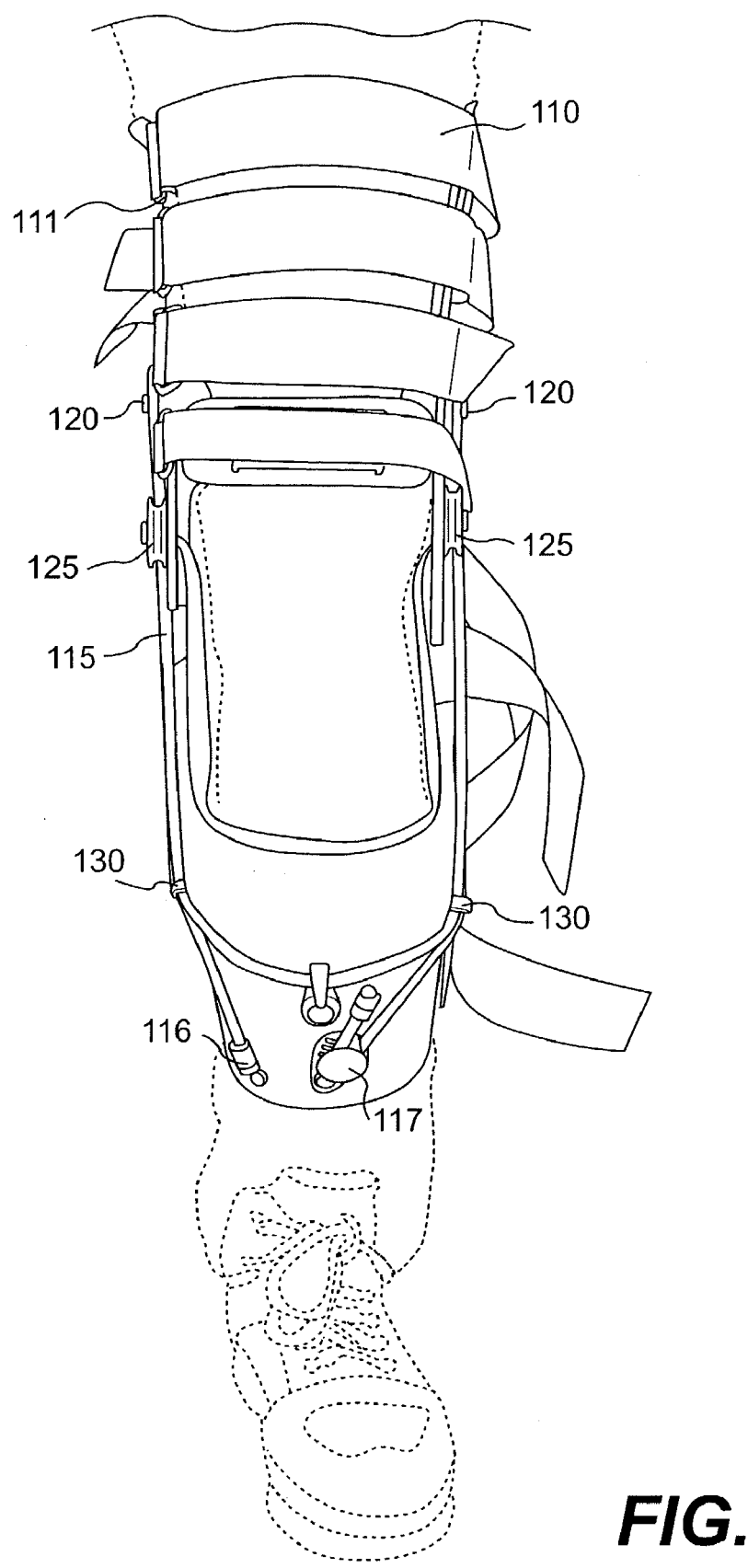

Three pairs of guides 120, 125 and 130 are also shown positioned on the support members 100 and 101. The side views (FIGS. 6 and 7) and perspective view (FIG. 5) only show one of the pair of guides 120, 125 and 130. FIG. 8 displays the three pairs of guides 120, 125 and 130 mounted on substantially opposite sides of the support members 100 and 101. Guides 120 are pulleys and are mounted on or near the sagittal plane 155 of the brace. Guides 130 are similarly placed on opposite sides of member 101. They are also placed substantially along the sagittal plane 155 of the brace. Guides 125 are placed on opposite sides of support member 100 near the axis 102. However, the guides 125 are mounted in the anterior portion 150 of support member 100.

Figure 5:
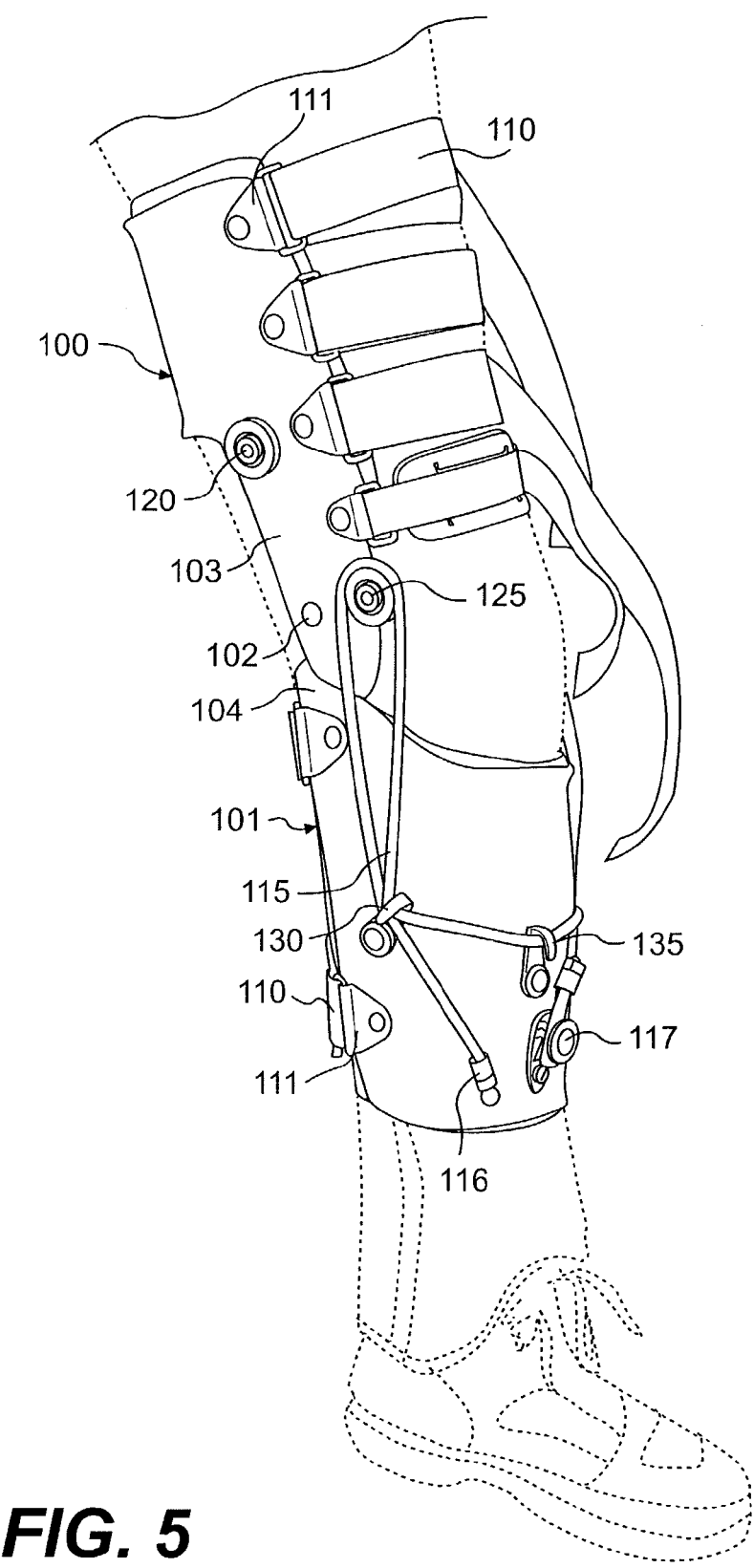
FIGS. 5 and 6 are perspective and side elevation views respectively of an alternative embodiment of a device in accordance with the present invention with the device shown in a position that creates an extension moment on a limb in the device.

FIGS. 5 and 6 demonstrate the use of the brace to create an extension moment. The tensioning member 115 is placed solely in guides 130 and around guides 125. In this way, because the tensioning member 115 is mounted around guide 125, a force is created to rotate the support members 100 and 101 in an extension direction. Similarly, as shown in FIGS. 7 and 8, when the tensioning member 115 is mounted solely through guides 120 and 130, a flexion moment is created, as the support members 100 and 110 are urged towards each other.

The geometry of the guides 120, 125 and 130 in relation to the tensioning member 115 is important and significant when determining variations for the placement of the guides on the support members 100 and 101. The guides may be placed in multiple locations to create the appropriate flexion and extension moments. For instance, guides 120 and 130 are shown as being mounted on opposite sides and at or near the sagittal plane 155. They could be mounted on either side of the sagittal plane 155 or further up or down the sagittal plane 155. Preferably, guides 120 are mounted higher (closer to the distal end of the support member) than guides 130. Still further alternatively, the guides 120 and/or 130 could be mounted in a slot (or star-shaped slot) that allows the location of the guides to be moved. This movement could be up and down in the sagittal plane. This movement could be into the anterior and posterior portions of the brace. However, the guides 125 must be mounted on the anterior portion of the brace so that when the tensioning member 115 is mounted solely in guides 125 and 130, the force of the tensioning member is in the anterior aspect of the device and moves to compel an extension moment. Also, the guides 120 and 130 must be placed so that when the tensioning member 115 is mounted solely around those pairs of guides, the tensioning member is aligned behind the hinge axis 102 and in the posterior aspect of the brace so as to create the flexion moment.

It should be noted here that, in the case of this knee brace, a flexion moment is created when the tensioning member is applying a force in the posterior aspect, while an extension moment is created by a force in the anterior aspect. The corresponding anterior and posterior forces in an elbow brace create the opposite flexion and extension moments respectively. This is the result of the different anatomical directions of bending of an elbow and a knee.

Guide 135 is merely a convenience for the apparatus. Typically, the tensioning member is looped through the guide 135 and around the guides 120 or 125. Then, the tensioning member is pulled around guides 130. The amount of tension in the tensioning member can be relatively substantial when considering the forces desirable for knee therapy. Also, as noted earlier, the tensioning member my be varied with respect to its length in order to increase or decrease the amount of flexion or extension moment created.

The use of pulleys as guides (for instance, guides 120 and 125) allows for the equalization of the force of tension that creates the flexion and tension moments. This allows for an equal, bilateral tension of the tensioning member 115 on the support members 100 and 101. If tension is not equalized (or if it is on only one side of a brace), then there is unequal force on the brace and, possibly, on the limb in the brace. The bilateral force of the displayed apparatus has beneficial therapeutic effect on the patient wearing the brace.

An alternative to the knee brace embodiment in FIGS. 5–8 is an orthotic device kit. Like the elbow brace discussed earlier herein, the kit includes all of the knee brace components and/or subcombinations thereof. Specifically, the kit includes first and second support members pivotally connected at their respective proximal ends by a pair of hinges mounted substantially on opposite sides of the support members. The hinges define a sagittal plane that divides each of the support members into anterior and posterior portions when the support members are in a substantially straight orientation. (See, e.g., FIG. 6). The kit includes a tensioning member. It also includes first and second pairs of guides adapted to be positioned on and at opposite sides of the first and second members respectively. A third pair of guides is adapted to be positioned on the first or second member near the proximal end of whichever member and on the anterior portion of that member. When the tensioning member is placed in the first and second pair of guides only, a flexion moment is created; and when the tensioning member is placed in the second and third pairs of guides only, an extension moment is created.

While the invention has been described with reference to specific embodiments thereof, it will understood that numerous variations, modifications and additional embodiments are possible, and accordingly, all such variations, modifications, and embodiments are to be regarded as being within the spirit and scope of the invention.

What is claimed is:

1. An orthotic device comprising:
   first and second elongated support members, wherein the support members are pivotally connected at their respective proximal ends by a pair of hinges mounted substantially on opposite sides of the support members, wherein each of the support members comprises anterior and posterior portions with respect to a sagittal plane passing through the hinges;
   a tensioning member;
   a first pair of guides positioned on the first member and substantially at opposite sides of the first member,
   a second pair of guides positioned on the second member and substantially along the sagittal plane and at opposite sides of the second member;
   a third pair of guides positioned on the first member near the proximal end of the first member and on the anterior portion of the first member;
   wherein, when the tensioning member is placed in the first and second pairs of guides only, a flexion moment is created; and when the tensioning member is placed in the second and third pairs of guides only, an extension moment is created.

2. An orthotic device as described in claim 1, wherein the tensioning member is a single, noncontinuous piece secured at each end to a support member.

3. An orthotic device as described in claim 1, wherein the tensioning member is a loop.

4. An orthotic device as described in claim 1, further comprising means for varying the length of the tensioning member.

5. An orthotic device as described in claim 1, wherein the tensioning member is an elastic cord.

6. An orthotic device as described in claim 1, wherein the tensioning member is a single, noncontinuous piece with one end fixed to a support member and the second end is variably attachable to a member, whereby the length of the member is variable.

7. An orthotic device as described in claim 1, wherein the hinges comprise range of pivot limiters.

8. An orthotic device as described in claim 5, further comprising a static cord connected to the support members and adapted to limit the range of pivot of the support members.

9. An orthotic device as described in claim 1, wherein the third pair of guides are pulleys.

10. An orthotic device as described in claim 1, wherein all of the guides are pulleys.

11. An orthotic device kit comprising:
   first and second elongated support members, wherein the support members are pivotally connected at their respective proximal ends by a pair of hinges mounted substantially on opposite sides of the support members, wherein each of the support members comprises anterior and posterior portions with respect to a sagittal plane passing through the hinges;
   a tensioning member;
   a first pair of guides adapted to be positioned on the first member and substantially at opposite sides of the first member,
   a second pair of guides adapted to be positioned on the second member and substantially along the sagittal plane and at opposite sides of the second member;
   a third pair of guides adapted to be positioned on the first member near the proximal end of the first member and on the anterior portion of that member;
   wherein, after the device is assembled, when the tensioning member is placed in the first and second pairs of guides only, a flexion moment is created; and when the tensioning member is placed in the second and third pairs of guides only, an extension moment is created.

* * * * *